United States Patent
Siddique et al.

(10) Patent No.: US 9,228,236 B2
(45) Date of Patent: *Jan. 5, 2016

(54) ALLELIC DISORDERS CAUSED BY MUTATIONS IN TRPV4

(71) Applicant: Northwestern University, Evanston, IL (US)

(72) Inventors: Teepu Siddique, Wilmette, IL (US); Han-Xiang Deng, Chicago, IL (US); Jianhua Yan, Naperville, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/792,850

(22) Filed: Mar. 11, 2013

(65) Prior Publication Data

US 2013/0183671 A1    Jul. 18, 2013

Related U.S. Application Data

(63) Continuation of application No. 12/974,209, filed on Dec. 21, 2010, now Pat. No. 8,394,589.

(60) Provisional application No. 61/288,710, filed on Dec. 21, 2009.

(51) Int. Cl.
| | | |
|---|---|---|
| C12Q 1/68 | (2006.01) | |
| C07H 21/02 | (2006.01) | |
| C07H 21/04 | (2006.01) | |

(52) U.S. Cl.
CPC ........ *C12Q 1/6883* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,011,769 A | 4/1991 | Duck et al. |
| 5,124,246 A | 6/1992 | Urdea et al. |
| 5,288,609 A | 2/1994 | Engelhardt et al. |
| 5,403,711 A | 4/1995 | Walder et al. |
| 5,409,818 A | 4/1995 | Davey et al. |
| 5,624,802 A | 4/1997 | Urdea et al. |
| 5,660,988 A | 8/1997 | Duck et al. |
| 5,710,264 A | 1/1998 | Urdea et al. |
| 5,780,223 A | 7/1998 | Lupski et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 7,727,717 B2 | 6/2010 | Vance et al. |
| 8,394,589 B2 * | 3/2013 | Siddique et al. ............ 435/6.11 |
| 2003/0092019 A1 | 5/2003 | Meyer et al. |

OTHER PUBLICATIONS

The Meriam Webster Dictionary definition for "Detect," printed on May 20, 2014, available via url: <merriam-webster.com/dictionary/detect>.*
GeneCard for the TRPV4 gene available via url: < genecards.org/cgi-bin/carddisp.pl?gene=TRPV4>, printed on Sep. 9, 2014.*
Vlam et al. Arch Neurol. Jun. 2012. 69: 790-791.*
Lucentini et al The Scientist (2004) vol. 18, p. 20.*
Hattersley et al. The Lancet. 2005. 366: 1315-1323.*
Hirschhorn et al. Genetics in Medicine. 2002. 4(2): 45-61.*
Antonellis et al. Glycyl tRNA synthetase mutations in Charcot-Marie-Tooth disease type 2D and distal spinal muscular atrophy type V. Am J Hum Genet 72, 1293-9 (2003).
Arniges et al., Human TRPV4 channel splice variants revealed a key role of ankyrin domains in multimerization and trafficking. J Biol Chem 281, 1580-6 (2006).
Barisic et al., Charcot-Marie-Tooth disease: a clinico-genetic confrontation. Ann Hum Genet 72(Pt 3):416-441 (2008).
Delong & Siddique. A large New England kindred with autosomal dominant neurogenic scapuloperoneal amyotrophy with unique features. Arch Neurol 49, 905-8 (1992).
Deng et al., Scapuloperoneal spinal muscular atrophy and CMT2C are allelic disorders caused by alterations in TRPV4, Nat Genet, 42(2):165-169 (2009).
D'Hoedt et al. Stimulus-specific modulation of the cation channel TRPV4 by PACSIN 3. J Biol Chem 283, 6272-80 (2008).
Dyck et al., Hereditary motor and sensory neuropathies. In: Peripheral Neuropathy (eds. P. J.Dyck, P. K.Thomas, J. W.Griffin, P. ALow & J. F.Poduslo), pp. 1094-1136. Philadelphia : W.B. Saunders Company (1993).

(Continued)

*Primary Examiner* — Carla Myers
(74) *Attorney, Agent, or Firm* — Foley & Lardner LLP

(57) ABSTRACT

The present invention provides methods, kits, and compositions for detecting mutations in transient receptor potential cation channel, subfamily V, member 4 (TRPV4). In particular, mutations are detected in TRPV4 to detect diseases such as scapuloperoneal spinal muscular atrophy (SPSMA) and hereditary motor and sensory neuropathy type IIC (HMSN IIC) or Charcot-Marie-Tooth disease type 2C (CMT2C).

2 Claims, 10 Drawing Sheets

(56) References Cited

OTHER PUBLICATIONS

Dyck et al. Hereditary motor and sensory neuropathy with diaphragm and vocal cord paresis. Ann Neurol 35, 608-15 (1994).

Evgrafov et al. Mutant small heat-shock protein 27 causes axonal Charcot-Marie-Tooth disease and distal hereditary motor neuropathy. Nat Genet 36, 602-6 (2004).

Fu et al., WNK kinases influence TRPV4 channel function and localization. Am J Physiol Renal Physiol 290, F1305-14 (2006).

Grynkiewicz et al., A new generation of Ca2+ indicators with greatly improved fluorescence properties. J Biol Chem 260, 3440-50 (1985).

Irobi et al. Hot-spot residue in small heat-shock protein 22 causes distal motor neuropathy. Nat Genet 36, 597-601 (2004).

Isozumi et al. Linkage of scapuloperoneal spinal muscular atrophy to chromosome 12q24.1-q24.31. Hum Mol Genet 5, 1377-82 (1996).

Jin et al., Structure of the N-terminal ankyrin repeat domain of the TRPV2 ion channel. J Biol Chem 281, 25006-10 (2006).

Klein et al. The gene for HMSN2C maps to 12q23-24: a region of neuromuscular disorders. Neurology 60, 1151-6 (2003).

Krakow et al. Mutations in the gene encoding the calcium-permeable ion channel TRPV4 produce spondylometaphyseal dysplasia, Kozlowski type and metatropic dysplasia. Am J Hum Genet 84, 307-15 (2009).

Liedtke & Friedman, Abnormal osmotic regulation in trpv4-/- mice. Proc Natl Acad Sci U S A 100, 13698-703 (2003).

Liedtke, Molecular mechanisms of TRPV4-mediated neural signaling. Ann N Y Acad Sci 1144, 42-52 (2008).

Liedtke et al. Vanilloid receptor-related osmotically activated channel (VR-OAC), a candidate vertebrate osmoreceptor. Cell 103, 525-35 (2000).

Liu et al. A role for AQP5 in activation of TRPV4 by hypotonicity: concerted involvement of AQP5 and TRPV4 in regulation of cell vol. recovery. J Biol Chem 281, 15485-95 (2006).

McEntagart et al. Confirmation of a hereditary motor and sensory neuropathy IIC locus at chromosome 12q23-q24. Ann Neurol 57, 293-7 (2005).

Nilius et al., Transient receptor potential cation channels in disease. Physiol Rev 87, 165-217 (2007).

Pedersen et al., TRP channels: an overview. Cell Calcium 38, 233-52 (2005).

Phelps et al., Structural analyses of the ankyrin repeat domain of TRPV6 and related TRPV ion channels. Biochemistry 47, 2476-84 (2008).

Quinzii et al. X-linked dominant scapuloperoneal myopathy is due to a mutation in the gene encoding four-and-a-half-LIM protein 1. Am J Hum Genet 82, 208-13 (2008).

Ramser et al. Rare missense and synonymous variants in UBE1 are associated with X-linked infantile spinal muscular atrophy. Am J Hum Genet 82, 188-93 (2008).

Rock et al. Gain-of-function mutations in TRPV4 cause autosomal dominant brachyolmia. Nat Genet 40, 999-1003 (2008).

Sidhaye et al. Transient receptor potential vanilloid 4 regulates aquaporin-5 abundance under hypotonic conditions. Proc Natl Acad Sci U S A 103, 4747-52 (2006).

Strotmann et al., OTRPC4, a nonselective cation channel that confers sensitivity to extracellular osmolarity. Nat Cell Biol 2, 695-702 (2000).

Suzuki et al., Impaired pressure sensation in mice lacking TRPV4. J Biol Chem 278, 22664-8 (2003).

Tang et al. Small heat-shock protein 22 mutated in autosomal dominant Charcot-Marie-Tooth disease type 2L. Hum Genet 116, 222-4 (2005).

Van Der Vleuten et al., Localisation of the gene for a dominant congenital spinal muscular atrophy predominantly affecting the lower limbs to chromosome 12q23-q24, Eur J Hum Genet, 6(4):376-382 (1998).

Wang et al. OS-9 regulates the transit and polyubiquitination of TRPV4 in the endoplasmic reticulum. J Biol Chem 282, 36561-70 (2007).

Wegierski et al. The HECT ubiquitin ligase AIP4 regulates the cell surface expression of select TRP channels. EMBO J 25, 5659-69 (2006).

Wissenbach et al., Trp12, a novel Trp related protein from kidney. FEBS Lett 485, 127-34 (2000).

Rock et al., "Gain of function mutations in TRPV4 cause autosomal dominant brachyolmia," Nature Genetics, 2008, 40:999-1003.

Gene Card for TRPV4 http://www.genecards.org/cgi-bin/carddisp.pl?gene=TRPV4&search=trpv4, accessed Jan. 17, 2012, 18 pages.

Mummidi et al., "Evolution of human and non-human primate CC chemokine receptor 5 gene and mRNA," J Biol Chem., 2000, 275:18946-18961.

Deng et al., "Scapuloperoneal Spinal Muscular Atrophy and Hereditary Motor and Sensory Neuropathy Type 2C are Allelic Disorders Caused by Mutations in the TRPV4 Gene," Annals of Neurology, 2009, 66(Suppl 13):S54. 134th Annual Meeting of the American Neurological Association, Baltimore, MD Oct. 11-14, 2009.

Kohler, G. et al., "Continuous Cultures of Fused Cells Secreting Antibody of Predefined Specificity," (1975) *Nature* 256:495-497.

Kozbor et al., "The Production of Monoclonal Antibodies from Human Lymphocytes," Immunol. Today, p. 72-79, vol. 4 (1993).

Barany, "Genetic disease detection and DNA amplification using cloned thermostable ligase," *Proc. Natl. Acad. Sci.*, vol. 88, pp. 189-193 (1991).

* cited by examiner

```
                           SEQUENCE LISTING

<160> NUMBER OF SEQ ID NOS: 7

<210> SEQ ID NO 1
<211> LENGTH: 58
<212> TYPE: PRT
<213> ORGANISM: Homo sapiens

<400> SEQUENCE: 1

Val His Ala Gln Ala Arg Gly Arg Phe Phe Gln Pro Lys Asp Glu Gly
1               5                   10                  15

Gly Tyr Phe Tyr Phe Gly Glu Leu Pro Leu Ser Leu Ala Ala Cys Thr
            20                  25                  30

Asn Gln Pro His Ile Val Asn Tyr Leu Thr Glu Asn Gly His Lys Lys
        35                  40                  45

Ala Asp Met Arg Arg Gln Asp Ser Arg Gly
    50                  55

<210> SEQ ID NO 2
<211> LENGTH: 58
<212> TYPE: PRT
<213> ORGANISM: Canis lupus familiaris

<400> SEQUENCE: 2

Val His Ala Gln Ala Arg Gly Arg Phe Phe Gln Pro Lys Asp Glu Gly
1               5                   10                  15

Gly Tyr Phe Tyr Phe Gly Glu Leu Pro Leu Ser Leu Ala Ala Cys Thr
            20                  25                  30

Asn Gln Pro His Ile Val Asn Tyr Leu Thr Glu Asn Gly His Lys Lys
        35                  40                  45

Ala Asp Met Arg Arg Gln Asp Ser Arg Gly
    50                  55

<210> SEQ ID NO 3
<211> LENGTH: 58
<212> TYPE: PRT
<213> ORGANISM: Bos taurus

<400> SEQUENCE: 3

Val His Ala Gln Ala Arg Gly Arg Phe Phe Gln Pro Lys Asp Glu Gly
1               5                   10                  15

Gly Tyr Phe Tyr Phe Gly Glu Leu Pro Leu Ser Leu Ala Ala Cys Thr
            20                  25                  30

Asn Gln Pro His Ile Val Asn Tyr Leu Thr Glu Asn Gly His Lys Lys
        35                  40                  45

Ala Asp Met Arg Arg Gln Asp Ser Arg Gly
    50                  55

<210> SEQ ID NO 4
<211> LENGTH: 58
<212> TYPE: PRT
<213> ORGANISM: Mus musculus

<400> SEQUENCE: 4

Val His Ala Gln Ala Arg Gly Arg Phe Phe Gln Pro Lys Asp Glu Gly
1               5                   10                  15

Gly Tyr Phe Tyr Phe Gly Glu Leu Pro Leu Ser Leu Ala Ala Cys Thr
```

```
                    20                  25                  30
Asn Gln Pro His Ile Val Asn Tyr Leu Thr Glu Asn Gly His Lys Lys
            35                  40                  45

Ala Asp Met Arg Arg Gln Asp Ser Arg Gly
    50                  55

<210> SEQ ID NO 5
<211> LENGTH: 58
<212> TYPE: PRT
<213> ORGANISM: Rattus norvegicus

<400> SEQUENCE: 5

Val His Ala Gln Ala Arg Gly Arg Phe Phe Gln Pro Lys Asp Glu Gly
1               5                   10                  15

Gly Tyr Phe Tyr Phe Gly Glu Leu Pro Leu Ser Leu Ala Ala Cys Thr
                20                  25                  30

Asn Gln Pro His Ile Val Asn Tyr Leu Thr Glu Asn Gly His Lys Lys
            35                  40                  45

Ala Asp Met Arg Arg Gln Asp Ser Arg Gly
    50                  55

<210> SEQ ID NO 6
<211> LENGTH: 58
<212> TYPE: PRT
<213> ORGANISM: Gallus gallus

<400> SEQUENCE: 6

Val His Ala Gln Ala Arg Gly Arg Phe Phe Gln Pro Lys Asp Glu Gly
1               5                   10                  15

Gly Tyr Phe Tyr Phe Gly Glu Leu Pro Leu Ser Leu Ala Ala Cys Thr
                20                  25                  30

Asn Gln Pro His Ile Val His Tyr Leu Thr Glu Asn Gly His Lys Gln
            35                  40                  45

Ala Asp Leu Arg Arg Gln Asp Ser Arg Gly
    50                  55

<210> SEQ ID NO 7
<211> LENGTH: 58
<212> TYPE: PRT
<213> ORGANISM: Danio rerio

<400> SEQUENCE: 7

Val His Ala Gln Ala Arg Gly Arg Phe Phe Gln Pro Arg Asp Glu Gly
1               5                   10                  15

Gly Tyr Phe Tyr Phe Gly Glu Leu Pro Leu Ser Leu Ala Ala Cys Thr
                20                  25                  30

Asn Gln Pro Asp Met Val His Tyr Leu Thr Glu Asn Gly His Lys Lys
            35                  40                  45

Ala Asp Leu Arg Arg Gln Asp Ser Arg Gly
    50                  55
```

ALLELIC DISORDERS CAUSED BY MUTATIONS IN TRPV4

CROSS-REFERENCE TO RELATED APPLICATION

The present application is a continuation of U.S. patent application Ser. No. 12/974,209, filed Dec. 21, 2010, now U.S. Pat. No. 8,394,589, which claims priority to U.S. Provisional Application 61/288,710 filed Dec. 21, 2009, each of which is herein incorporated by reference in its entirety.

STATEMENT REGARDING FEDERALLY SPONSORED RESEARCH OR DEVELOPMENT

This invention was made with government support under Grant No. NS050641 awarded by the National Institutes of Health. The government has certain rights in the invention.

FIELD OF THE INVENTION

The present invention provides methods, kits, and compositions for detecting mutations in transient receptor potential cation channel, subfamily V, member 4 (TRPV4). In particular, mutations are detected in TRPV4 to detect diseases such as scapuloperoneal spinal muscular atrophy (SPSMA) and hereditary motor and sensory neuropathy type IIC (HMSN IIC) or Charcot-Marie-Tooth disease type 2C (CMT2C).

BACKGROUND

Scapuloperoneal spinal muscular atrophy (SPSMA) and hereditary motor and sensory neuropathy type IIC (HMSN IIC) or Charcot-Marie-Tooth disease type 2C (CMT2C) are phenotypically heterogeneous disorders involving topographically distinct nerves and muscles. Scapuloperoneal syndromes can resemble facioscapulohumeral muscular dystrophy (FSH) due to scapular weakness or HMSN (or CMT) due to atrophy of peroneal muscles. In a large New England kindred of French-Canadian origin, Delong and Siddique identified 20 individuals in five generations affected with a neurogenic scapuloperoneal amyotrophy (DeLong and Siddique, 1992; herein incorporated by reference in its entirety). The disease is transmitted as an autosomal dominant trait and is characterized by congenital absence of muscles, developmental abnormalities of the bones, progressive scapuloperoneal atrophy and weakness, and laryngeal palsy eventually requiring permanent tracheostomy. On account of the distinct topographical distribution of muscle weakness and atrophy, it was considered a form of scapuloperoneal spinal muscular atrophy (SPSMA) (DeLong and Siddique, 1992; herein incorporated by reference in its entirety). Using genetic linkage analysis of this kindred, Isozumi et al. and mapped the SPSMA locus to chromosome 12q24.1-q24.31 within a 14 Mb interval between D12S338 and D12S366, with a two-point lod score of 6.67 and multipoint lod scores of 7.38 (Isozumi et al., 1996; herein incorporated by reference in its entirety).

HMSN or CMT is the most common inherited peripheral neuropathy. It includes a group of clinically and genetically heterogeneous hereditary neuropathies that share clinical characteristics of progressive distal muscle weakness and atrophy, foot deformities, distal sensory loss, and depressed or absent tendon reflexes. It can be categorized according to its clinical, electrophysiological or pathological features, transmission patterns, age of disease onset, and molecular pathology. It may appear as HMSN if muscle weakness is predominant with mild sensory deficits; distal hereditary motor neuropathy (dHMN) if the motor deficit is dominant; and hereditary sensory neuropathy (HSN) or hereditary sensory and autonomic neuropathy (HSAN) if sensory deficits and/or autonomic dysfunctions predominate (Dyck et al., 1993; Barisic et al., 2008; herein incorporated by reference in their entireties). HMSN or CMT is associated with more than 30 loci and at least 20 causative genes (see web sites for molgen.ua.ac.be/CMTMutations/; and neuro.wustl.edu/neuromuscular/time/hmsn.html; herein incorporated by reference in their entireties). Two kindreds were described with an autosomal dominant inherited disorder characterized by a variable degree of muscle weakness of limbs, vocal cords, and intercostal muscles and by asymptomatic sensory impairment in some cases (Dyck et al., 1994; herein incorporated by reference in its entirety). Life expectancy in the patients was shortened because of respiratory failure or complications. Because nerve conduction velocities were normal and the disorder represented an inherited axonal neuropathy, this condition was classified as a form of HMSN type II. Linkage analysis using the large Kinship 1, an American kindred of English and Scottish descent, excluded the loci of CMT1A (HMSN IA) and the CMT1B (HMSN IB) in this pedigree (Dyck et al., 1994; herein incorporated by reference in its entirety). This new form of autosomal dominant HMSN was assigned as HMSN IIC or CMT2C. The relationship of Kinship 1 was reexamined and 5 additional affected members were identified (Klein et al., 2003; herein incorporated by reference in its entirety). Using a genome wide scan approach and linkage analysis, it was established the locus of the HMSN IIC, or CMT2C to a 5.7 Mb region between D12S105 and D12S1330, with a lod score of 5.17 (Klein et al., 2003; herein incorporated by reference in its entirety). Subsequently, the CMT2C locus was further refined to a 4 Mb region between S12S105 and S12S1340, with a combined lod score of 2.1 using two relatively small families (McEntagart et al., 2005; herein incorporated by reference in its entirety).

The diagnosis of SPSMA and CMT2C is made qualitatively based on an assessment of clinical, electrophysiological and/or pathological features, transmission patterns, and age of a disease onset. What is needed is a molecular genetics tool available for a definitive diagnosis.

SUMMARY OF THE INVENTION

In some embodiments, the present invention provides methods of detecting a disease by detecting mutations in TRPV4, wherein said disease is selected from: scapuloperoneal spinal muscular atrophy (SPSMA) and hereditary motor and sensory neuropathy type IIC (HMSN IIC) or Charcot-Marie-Tooth disease type 2C (CMT2C).

In some embodiments, the present invention provides methods of detecting a disease in a subject by detecting mutations in TRPV4, wherein the disease is a TRPV4 peripheral neuropathy and bony displasia. In some embodiments, the TRPV4 peripheral neuropathy and bony displasia is selected from: scapuloperoneal spinal muscular atrophy and hereditary motor and sensory neuropathy type IIC or Charcot-Marie-Tooth disease type 2C. In some embodiments, the mutations in TRPV4 are selected from TRPV4-R269H and TRPV4-R316C. In some embodiments, the subject is asymptomatic. In some embodiments, the subject displays symptoms indicative of one or more types of TRPV4 peripheral neuropathy and bony dysplasia. In some embodiments, the mutations in TRPV4 are detected by exposing a subject sample to a detection reagent, and detecting the presence of mutations in TRPV4 in the sample.

In some embodiments, the present invention provides methods for identifying a subject as a carrier of TRPV4 peripheral neuropathy and bony displasia, comprising detecting the presence of mutations in TRPV4 in a sample from the subject. In some embodiments, the mutations in TRPV4 are detected by exposing a sample from the subject to a detection reagent, and detecting the presence of mutations in TRPV4 in the sample. In some embodiments, the TRPV4 peripheral neuropathy and bony displasia is selected from: scapuloperoneal spinal muscular atrophy and hereditary motor and sensory neuropathy type IIC or Charcot-Marie-Tooth disease type 2C. In some embodiments, the mutations in TRPV4 are selected from TRPV4-R269H and TRPV4-R316C. In some embodiments, the subject is asymptomatic. In some embodiments, the subject will not develop TRPV4 peripheral neuropathy and bony dysplasia, but is capable of passing it on to offspring.

In some embodiments, the present invention provides a method for identifying compositions effective in treating or preventing TRPV4 peripheral neuropathy and bony displasia, comprising: identifying compositions capable of inhibiting, suppressing, and/or replacing the lost effects of mutations in the TRPV4.

Embodiments of the present invention provide methods for treatment and/or prevention of TRPV4-PNAB disorders (e.g. SPSMA, HMSN IIC, CMT2C, etc.) by targeting mutations in the TRPV4 gene or TRPV4, or the downstream products thereof (e.g. proteins, pathways, etc.). In some embodiments, the present invention provides compositions for treatment and/or prevention of TRPV4-PNAB disorders (e.g. SPSMA, HMSN IIC, CMT2C, etc.). In some embodiments, the present invention provides compositions (e.g. proteins (e.g. antibodies, replacement proteins, etc.), small molecules (e.g. pharmaceuticals), nucleic acids (e.g. siRNA, miRNA, gene therapy, etc.), etc.) that target mutations in the TRPV4 gene or TRPV4, or the downstream products thereof (e.g. proteins, pathways, etc.). In some embodiments, the present invention provides compositions that inhibit expression of mutant TRPV4 genes or suppress the function of mutant TRPV4 or the downstream products thereof (e.g. proteins, pathways, etc.). In some embodiments, the present invention provides compositions that replace the aberrant function of mutant TRPV4 genes or TRPV4, or downstream products thereof (e.g. proteins, pathways, etc.).

Embodiments of the present invention provide compositions, methods, and assays for screening therapeutics (e.g. proteins (e.g. antibodies, replacement proteins, etc.), small molecules (e.g. pharmaceuticals), nucleic acids (e.g. siRNA, miRNA, gene therapy, etc.), etc.) to treat and/or prevent TRPV4-PNAB disorders (e.g. SPSMA, HMSN IIC, CMT2C, etc.). In some embodiments, compositions are screened for effectiveness in treating and/or preventing TRPV4-PNAB disorders (e.g. SPSMA, HMSN IIC, CMT2C, etc.) based on their affinity to, suppression of, or replacement of mutant TRPV4 genes or TRPV4, or downstream products thereof (e.g. proteins, pathways, etc.).

The mutant TRPV4 genes and/or mutant TRPV4 of the present disclosure, including fragments, derivatives and analogs thereof, may be used as immunogens to produce antibodies having use in the diagnostic, screening, research, and therapeutic methods. The antibodies may be polyclonal or monoclonal, chimeric, humanized, single chain, Fv or Fab fragments. Various procedures known to those of ordinary skill in the art may be used for the production and labeling of such antibodies and fragments. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975). Antibodies or fragments exploiting the differences between mutant TRPV4 genes or mutant TRPV4 and their wild-type counterparts are provided.

The present disclosure provides DNA, RNA and protein based diagnostic and screening methods that either directly or indirectly detect mutant TRPV4 genes or mutant TRPV4. The present disclosure also provides compositions and kits for diagnostic and screening purposes. In some embodiments, the diagnostic and screening methods may be qualitative or quantitative. In some embodiments, the diagnostic and screening methods may be conducted in vitro or in vivo. In some embodiments, the diagnostic and screening methods may comprise nucleic acid detection involving, for example: DNA amplification (e.g. PCR), sequencing, hybridization techniques (e.g. In situ hybridization), etc. In some embodiments, the diagnostic and screening methods may comprise protein detection involving, for example: protein sequencing, immunoassays (e.g., Western blot, ELISA, immunohistochemisty, etc.), flow cytometry, mass spectrometry, etc. In some embodiments, high through-put molecular screening techniques are provided to identify compositions targeting mutant TRPV4 genes or mutant TRPV4. In some embodiments, detection of mutant TRPV4 genes or mutant TRPV4 is provided by in vivo imaging techniques, including but not limited to: radionuclide imaging; positron emission tomography (PET); computerized axial tomography, X-ray or magnetic resonance imaging methods, fluorescence detection, and chemiluminescent detection.

The present disclosure contemplates the generation of transgenic animals comprising mutant TRPV4 genes or mutants and variants thereof (e.g., truncations or single nucleotide polymorphisms). In preferred embodiments, the transgenic animal displays an altered phenotype (e.g., increased or decreased presence TRPV4-PNAB disorders) as compared to wild-type or other mutant animals. Methods for analyzing the presence or absence of such phenotypes are provided.

Any of these compositions, alone or in combination with other compositions of the present disclosure, may be provided in the form of a kit.

In certain embodiments, the present invention provides compositions comprising a nucleic acid detection assay configured to identify at least one mutation is selected from TRPV4-R269H and TRPV4-R316C, wherein said nucleic acid detection assay comprises at least one oligonucleotide (e.g., primer, probe, INVADER oligo, etc.) and at least one enzyme (e.g., polymerase, kinase, FEN-1, etc.). Numerous types of nucleic acid detection assays are known in the art as described below. In certain embodiments, the nucleic acid detection assay comprises a pair of primers configured to amplify a portion of TRPV4 that contains position 269 and/or position 316. In other embodiments, the nucleic acid detection assay further comprises a polymerase and a probe specific for the TRPV4-R269H or TRPV4-R316C mutations.

The methods, systems, and compositions of the present invention may be employed with any nucleic acid detection assay. For example, the methods, systems, and applications of the present invention may find use in detection assays that include, but are not limited to, enzyme mismatch cleavage methods (e.g., Variagenics, U.S. Pat. Nos. 6,110,684, 5,958, 692, 5,851,770, herein incorporated by reference in their entireties); polymerase chain reaction; branched hybridization methods (e.g., Chiron, U.S. Pat. Nos. 5,849,481, 5,710, 264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); FULL-VELOCITY assays; and sandwich hybridization methods (e.g., U.S. Pat. No. 5,288,609, herein incorporated by reference in its entirety); the INVADER assay (Third Wave Technologies) and are described in U.S. Pat. Nos. 5,846,717, 5,985,557, 5,994,069, 6,001,567, and 6,090,543, as well as sequencing methods (including so called next-generation sequencing methodologies).

DETAILED DESCRIPTION

Experiments conducted during development of embodiments of the present invention demonstrate that mutations in the TRPV4 gene, for example TRPV4-R269H and/or TRPV4-R316C, cause the genetically inherited TRPV4-PNAB disorders (e.g. SPSMA, HMSN IIC, CMT2C, etc.). The present invention provides methods, kits, and compositions for detecting mutations in transient receptor potential cation channel, subfamily V, member 4 (TRPV4). In particular, mutations are detected in TRPV4 to detect diseases such as scapuloperoneal spinal muscular atrophy (SPSMA) and hereditary motor and sensory neuropathy type IIC (HMSN IIC) or Charcot-Marie-Tooth disease type 2C (CMT2C). In some embodiments, the present invention provides method for detecting TRPV4-associated peripheral neuropathy and bony dysplasia (TRPV4-PNAB). In some embodiments, TRPV4-PNAB comprises clinically distinct, but sometimes overlapping phenotypes of diseases associated with TRPV4 mutations (e.g. SPSMA and HMSN IIC or CMT2C, etc.). In some embodiments, the present invention provides genetic testing to identify subjects as carriers of one or more TRPV4-PNAB disorders. In some embodiments, the present invention provides screening of compounds (e.g. peptides, nucleic acids, small molecules, etc.) for the treatment and/or prevention of one or more TRPV4-PNAB disorders. In some embodiments, the present invention provides compositions (e.g. peptides, nucleic acids, small molecules, etc.) and methods for the treatment and/or prevention of one or more TRPV4-PNAB disorders.

Experiments conducted during the development of the present invention identified that mutations in TRPV4 are causes for both scapuloperoneal spinal muscular atrophy (SPSMA) and hereditary motor and sensory neuropathy type IIC (HMSN IIC) or Charcot-Marie-Tooth disease type 2C (CMT2C). Although the present invention is not limited to any particular mechanism of action and an understanding of the mechanism of action is not necessary to practice the present invention, functional analysis revealed that an increased calcium channel activity in response to the agonist arachidonic acid is a distinct property of both SPSMA- and CMT2C-causing mutants. In some embodiments, the present invention provides genetic tools for diagnosis of SPSMA and CMT2C. In some embodiments, the present invention provides a pathophysiological basis for design and/or selection of therapeutics targeting SPSMA and/or CMT2C.

Figure 1:
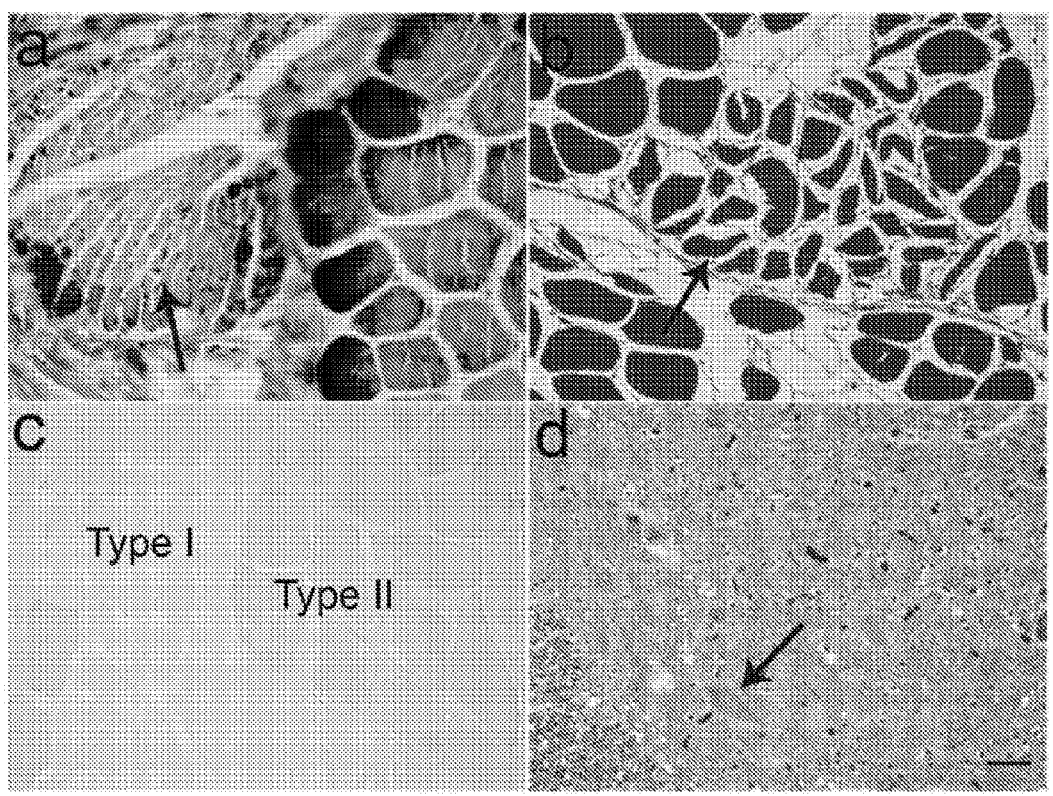
FIG. 1 shows images of pathology of a patient with SPSMA: (a) phosphotungstic acid hematoxylin (PTAH) staining of muscle biopsy showing severe muscle fiber type grouping and atrophy (arrow), (b) H&E staining of muscle autopsy sample showing severe muscle fiber type grouping and atrophy (arrow), (c) ATPase staining (pH 9.4) of muscle autopsy samples showing both small type 1 and type 2 fibers and fiber type grouping, and (d) Luxol fast blue/H&E staining of spinal cord sections showing a normal number of anterior horn cells (a representative motor neuron in the anterior horn is indicated by an arrow).
Figure 7:
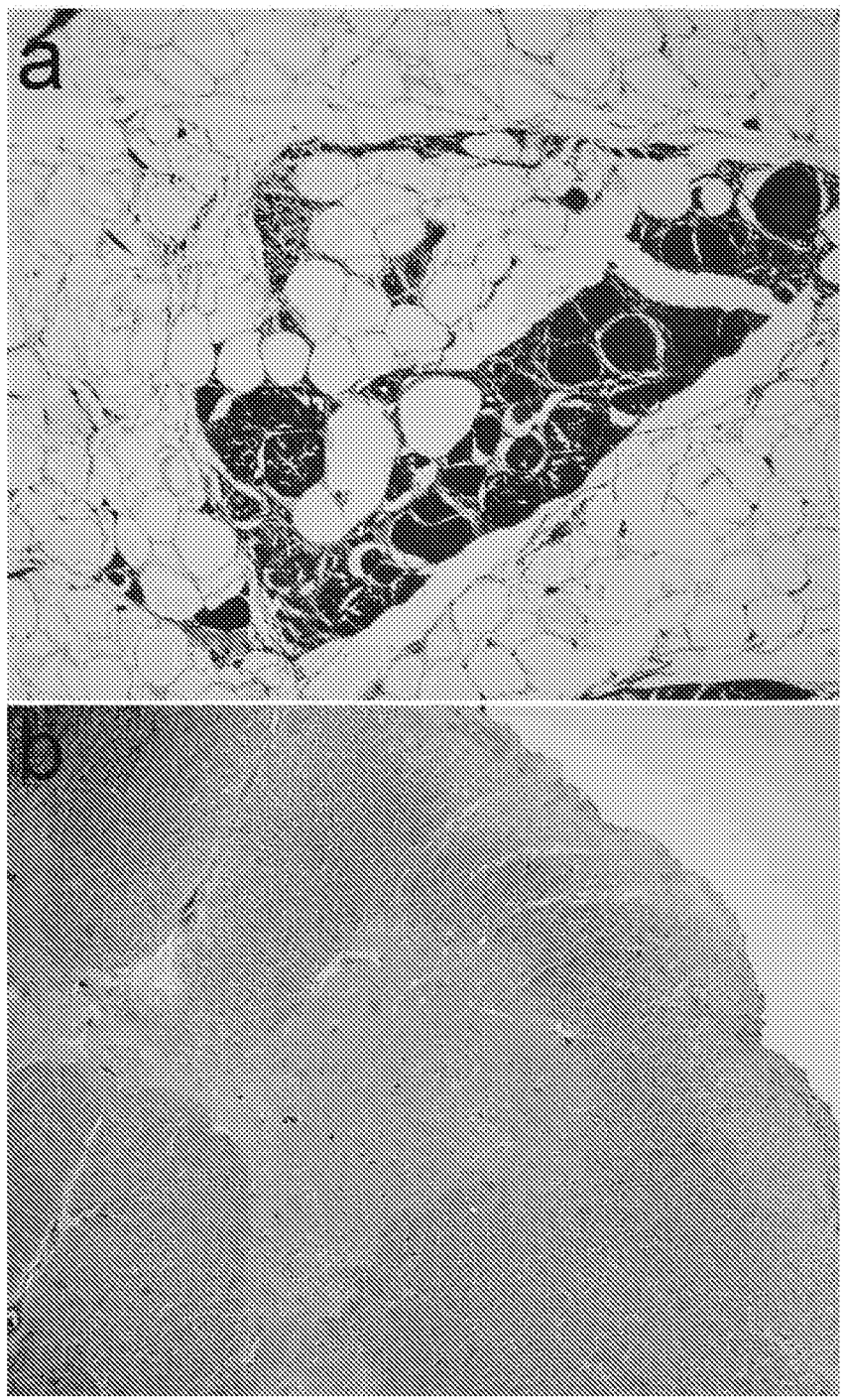
FIG. 7 shows images of pathology of a patient with SPSMA: (a) Muscle autopsy samples showing extensive fatty replacement, increased endomysial fibrosis, severe muscle type grouping and atrophy, marked variability of fiber size, and many fibers with multiple internal nuclei, fiber splitting, and multiple nuclear bags. (b) Luxol fast blue/H&E staining of spinal cord sections from the autopsy sample revealed a normal number of motor neurons in the motor cortex and spinal cord. The lateral corticospinal tracts were well preserved.

SPSMA is characterized by progressive scapuloperoneal atrophy and weakness, laryngeal palsy, congenital absence of muscles, and developmental abnormalities of the bones (DeLong & Siddique *Arch Neurol* 49, 905-8 (1992); herein incorporated by reference in its entirety). Pathological studies of biopsy and autopsy samples from a SPSMA patient revealed severe muscle fiber type grouping and atrophy (SEE FIG. 1a-c), extensive fatty replacement, increased endomysial fibrosis, marked variability of fiber size, and many fibers with multiple internal nuclei, fiber splitting, and multiple nuclear bags (SEE FIGS. 1a-c and 7a). Both type 1 and type 2 fibers showed atrophy as demonstrated by ATPase staining (SEE FIG. 1c). These pathological changes were particularly severe in the gastrocnemius muscle. However, spinal cord sections revealed normal numbers of motor neurons in the motor cortex and spinal cord. There was no gliosis in the anterior horns. The lateral corticospinal tracts were well preserved (SEE FIGS. 1d, and 7b). These findings, together with previous clinical and neurophysiological data support a diagnosis of spinal neurogenic amyotrophy due to peripheral motor neuropathy (DeLong & Siddique *Arch Neurol* 49, 905-8 (1992); herein incorporated by reference in its entirety). The entire 4 Mb CMT2C region is included in the 14 Mb SPSMA region, and SPSMA and CMT2C share a number of common clinical features, including characteristic vocal cord paresis (DeLong & Siddique. *Arch Neurol* 49, 905-8 (1992); Dyck et al. *Ann Neurol* 35, 608-15 (1994); Isozumi et al. *Hum Mol Genet* 5, 1377-82 (1996); Klein et al. *Neurology* 60, 1151-6 (2003); McEntagart et al. *Ann Neurol* 57, 293-7 (2005); herein incorporated by reference in their entireties).

Figure 2:
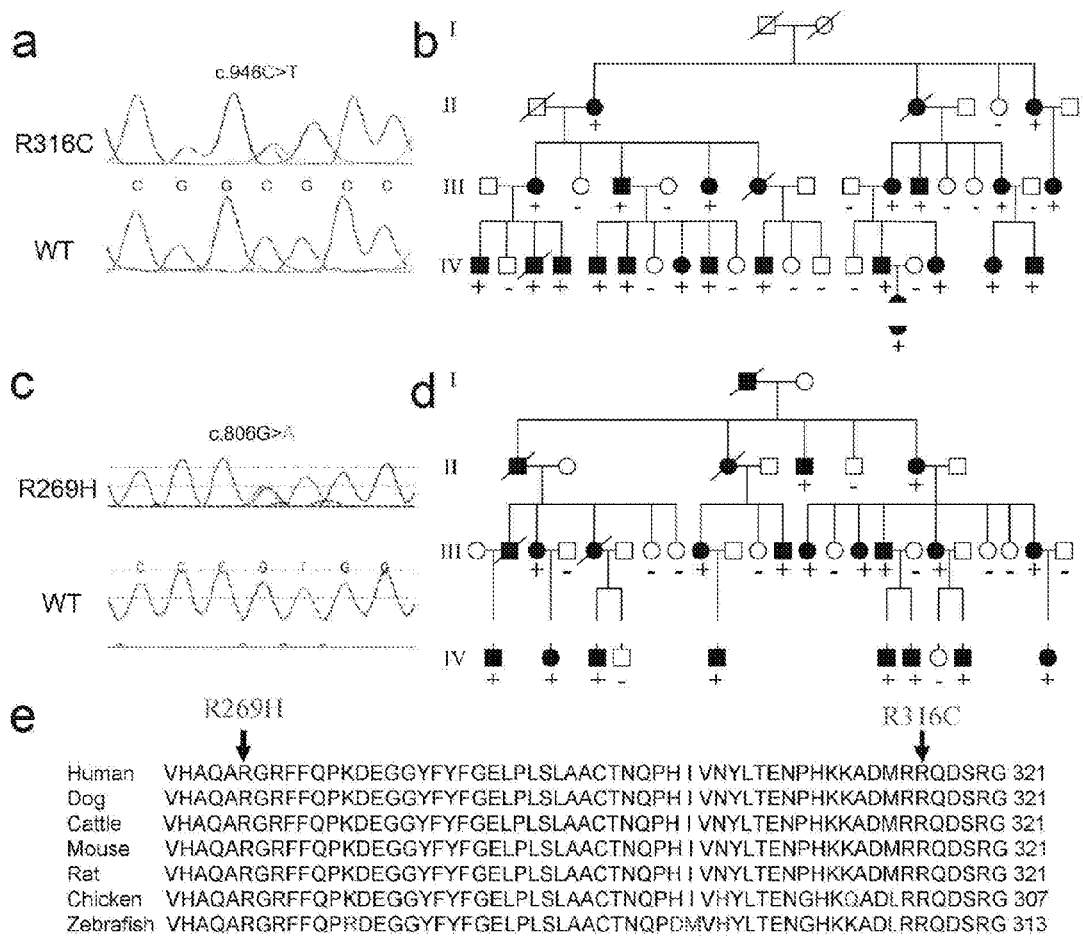
FIG. 2 shows mutations of the TRPV4 in SPSMA and CMT2C pedigrees. (a) A heterozygous mutation, c.946C>T, resulting in R316C, was identified in exon 6 of the TRPV4 gene in the SPSMA family. Wild type (WT) sequence is shown in the lower panel (SEQ ID NO:1). (b) All the affected members whose DNA samples were available for sequencing analysis had the R316C mutation. (c) A heterozygous mutation, c.806G>A, leading to R269H, in exon 5 of the TRPV4 gene was identified in the CMT2C family. Wild type (WT) sequence is shown in the lower panel. (d) All the affected members whose DNA samples were available for sequencing analysis had this R269H mutation. (e) Evolutionary conservation of amino acids in the mutated region of TRPV4 in different species. Comparison of human (*H. sapiens*; SEQ ID NO:1) TRPV4 and its orthologues in dog (*C. lupus* familiaris; SEQ ID NO:2), cattle (*B. taurus*; SEQ ID NO:3), mouse (*M. musculus*; SEQ ID NO:4), rat (*R. norvegicus*; SEQ ID NO:5), chicken (*G. gallus*; SEQ ID NO:6) and zebrafish (*D. rerio*; SEQ ID NO:7). Amino acids identical to human TRPV4 are in black letters and non-identical ones are denoted in red letters. The positions of the C-terminal amino acids are shown on the right. The mutated amino acids are indicated by arrows on the top. (+) indicates TRPV4 mutation and (−) indicates wild-type.

Experiments were conducted during development of embodiments of the present invention to determine whether SPSMA and CMT2C may be clinical variants of the same genetic entity. Experiments were conducted to excluded mutations in HSPB8, which is linked to distal hereditary motor neuropathy type (dHMN) II 6 or CMT2L 7 near the CMT2C locus. This work also excluded mutations in UBE3B, UBS30 and LIM homeobox 5 (LHX5), which shares homology to UBE1 or FHL1, as mutations in UBE1 and FHL1 are linked to infantile spinal muscular atrophy (Ramser et al. *Am J Hum Genet* 82, 188-93 (2008); herein incorporated by reference in its entirety) and scapuloperoneal myopathy (Quinzii et al. Am J Hum Genet 82, 208-13 (2008); herein incorporated by reference in its entirety), respectively. A total of 62 genes were sequenced, including all the 56 known and predicted genes in the minimum 4 Mb CMT2C region by using DNA samples from SPSMA patients. A heterozygous mutation was identified in the TRPV4 gene (Liedtke et al. Cell 103, 525-35 (2000); Strotmann et al. Nat Cell Biol 2, 695-702 (2000); Wissenbach et al. FEBS Lett 485, 127-34 (2000); herein incorporated by reference in its entirety). The mutation, c.946C>T, occurs in exon 6 and presumably results in an amino acid substitution of arginine by cysteine at codon 316 (R316C) (SEE FIG. 2a). The R316C mutation co-segregated with the disease in the large SPSMA pedigree (SEE FIG. 2b). This mutation was not present in the SNP database or in over 600 control samples. Other genetic variants were either polymorphisms and/or did not co-segregate with the disease. Thus, TRPV4-R316C is the only identified genetic defect in the encoding exons of all the genes within the minimum region shared by both the SPSMA and CMT2C in the SPSMA family.

Genetic analysis of the TRPV4 gene was extended to the original CMT2C family. Previous sequencing analysis of 45 genes in the CMT2C region had not revealed any pathogenic mutation. Analysis of the TRPV4 gene revealed a heterozygous mutation, c.806G>A, leading to R269H, in exon 5 of the TRPV4 gene in this large CMT2C pedigree (SEE FIG. 2c). The R269H mutation co-segregated with the disease in this family (SEE FIG. 2d). This mutation was not present in the SNP database and was not detected in over 700 control samples. Both the R316 and R269 residues of TRPV4 are conserved amino acids among human, rat, mouse, chicken, stickleback and zebra fish (SEE FIG. 2e).

Figure 3:
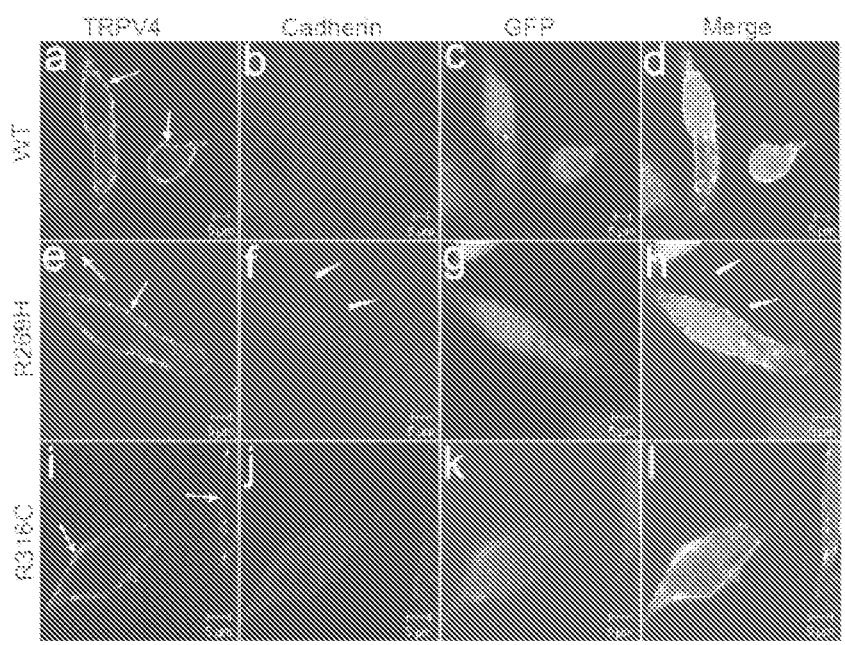
FIG. 3 shows images depicting localization of wild-type and mutant TRPV4 on the plasma membrane. Confocal microscopy was performed using HEK293 cells transfected with plasmids pIRES2-ZsGreen1 containing wtTRPV4 (a-d), TRPV4R269H (e-h) or TRPV4R316C (i-l). Cells expressing exogenous TRPV4 were labeled by green fluorescent protein (GFP) (c, g and k). TRPV4 is shown by blue (a, e and i) and cadherin by red (b, f and j). Merged images are shown on the right panels (d, h and l). Arrows indicate TRPV4 signals on the plasma membrane. Arrowheads indicate representative cells without significant expression of GFP as well as TRPV4 (f and h).
Figure 8:
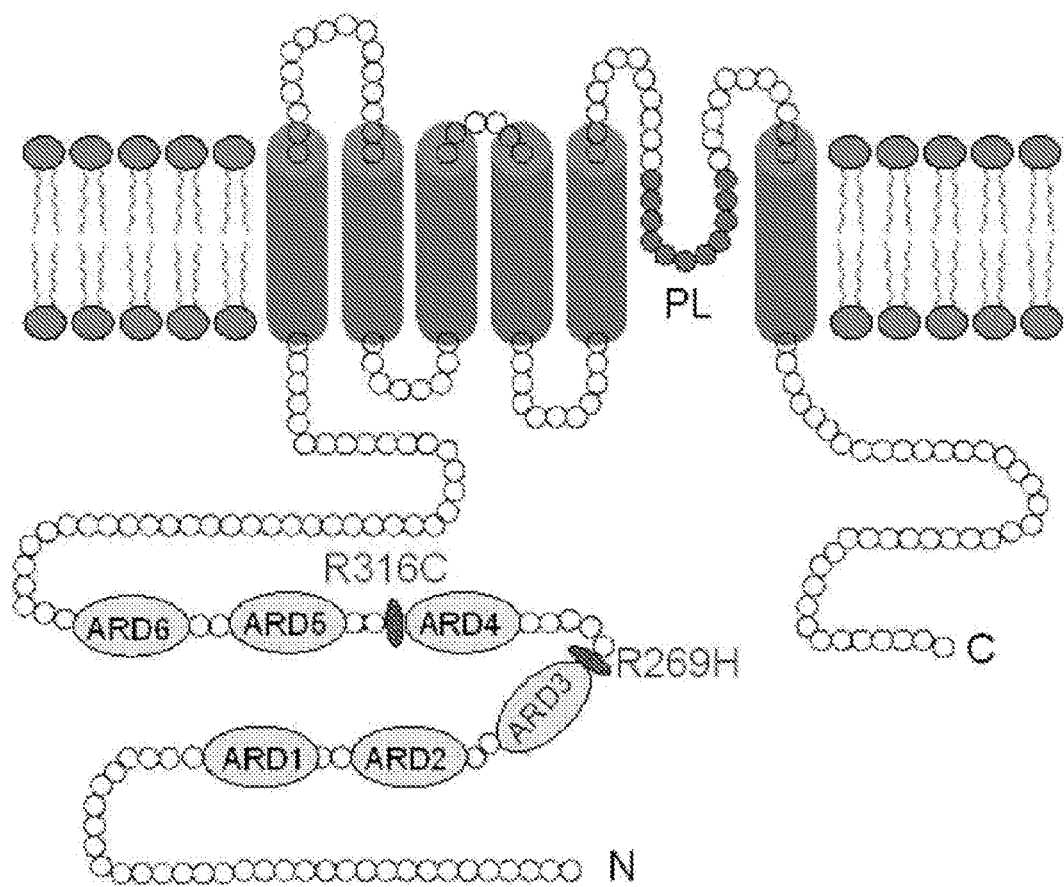
FIG. 8 shows the schematic model of TRPV4. The channel's core consists of six α-helical transmembrane domains and a pore loop (PL) flanked by TM5 and TM6 in the C-terminal part. Six ankyrin-repeat domains that have been shown to be a common structural feature in TRPV family near the N-terminus are individually labeled (ARD1-6). Mutations identified in the ARD-containing region are shown by red ovals.

Both R269H and R316C mutations occur in the ankyrin repeat-containing region of the cytoplasmic N-terminus, which usually mediates protein-protein interactions (SEE FIG. 8) (Jin et al. J Biol Chem 281, 25006-10 (2006); Phelps et al. Biochemistry 47, 2476-84 (2008); herein incorporated by reference in their entireties). TRPV4 splice variants affecting this region have shown defects in oligomerization, leading to accumulation of TRPV4 monomers in the endoplasmic reticulum (Arniges et al. *J Biol Chem* 281, 1580-6 (2006); herein incorporated by reference in their entireties). Since these variants are unable to be targeted to the plasma membrane, they are functionally inactive. To examine if the mutants have defects in subcellular trafficking, the subcellular distribution of the human wild-type TRPV4 (wtTRPV4)

and mutant TRPV4 with R269H (TRPV4R269H) or R316C (TRPV4R316C) mutation was analyzed in transiently transfected HEK293 cells. Exogenous TRPV4 was present on the plasma membrane. Both mutants had a similar pattern of subcellular localization to the wtTRPV4 in the transfected cells (SEE FIG. 3), indicating that these two mutations may not interfere with channel assembly and intracellular trafficking. This was supported by a cell surface biotinylation assay, which did not show significant difference in the level of TRPV4 at the plasma membrane between the wild-type and mutants.

Figure 4:
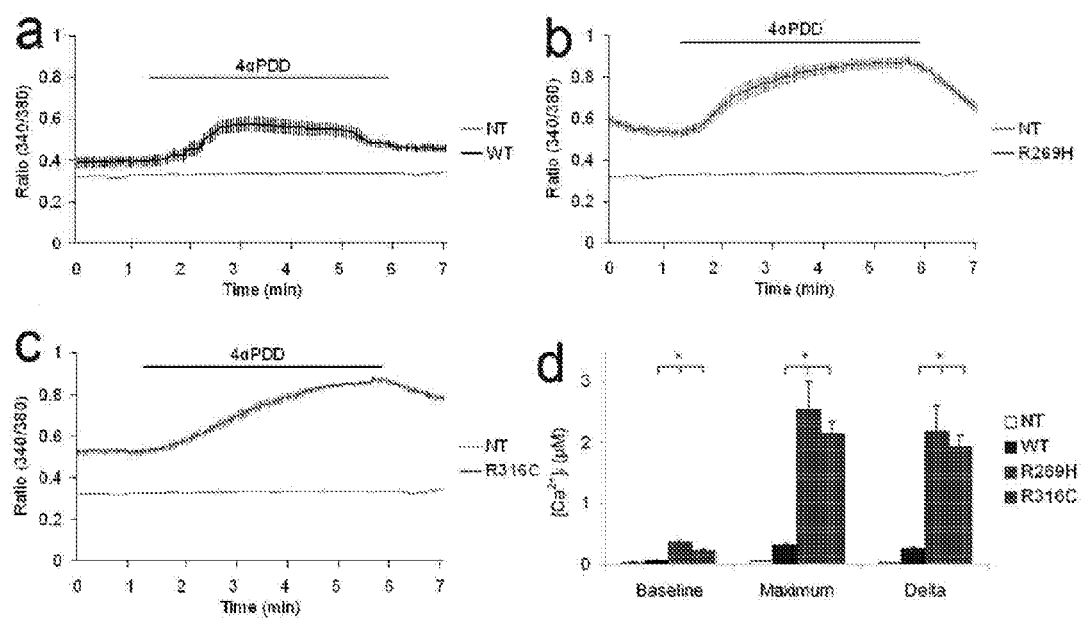
FIG. 4 shows the graphs depicting the effect of mutations on TRPV4 activity when stimulated with 4αPDD. Effect of stimulation with 4αPDD (2 μM) on internal fluorescence ratio in WT-TRPV4 (a), R269H (b) and R316C (c) transfected HEK293 cells. (d) Application of 4αPDD induced an increase in [Ca2+]i. Average increases, basal and maximum values are given.
Figure 5:
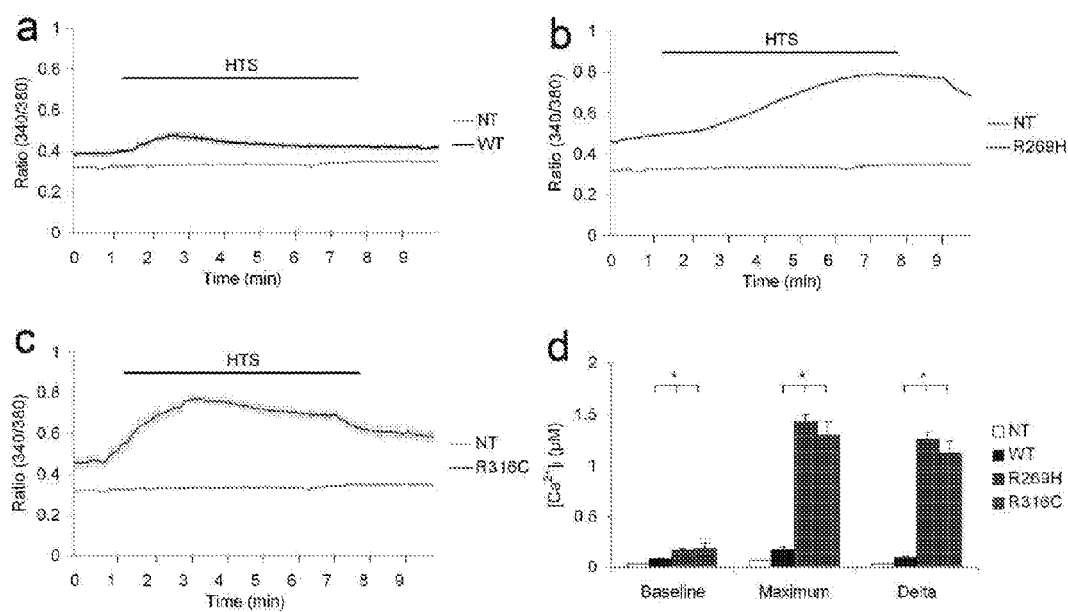
FIG. 5 shows graphs depicting the effect of mutations on TRPV4 activity when stimulated with hypotonic solution (HTS). Effect of stimulation with a hypotonic stimulus (HTS) (200 mOsm) on internal fluorescence ratio in WT-TRPV4 (a), R269H (b) and R316C (c) transfected HEK293 cells. (d) Application of HTS induced an increase in [Ca2+]i. Average increases, basal and maximum values are given.
Figure 9:
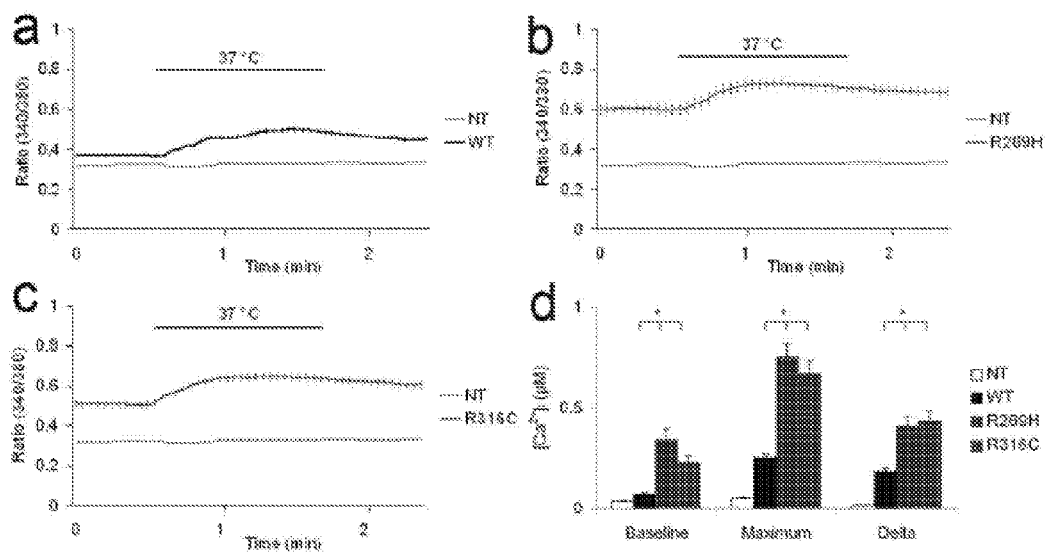
FIG. 9 shows the graphs depicting the effect of mutations on TRPV4 activity when stimulated with moderate heat. Effect of stimulation with a moderate thermal stimulus (37° C.) on internal fluorescence ratio in WT-TRPV4 (a), R269H (b) and R316C (c) transfected HEK293 cells. (d) Application of thermal stimulus induced an increase in $[Ca^{2+}]_i$. Average increases, basal and maximum values are given.
Figure 10:
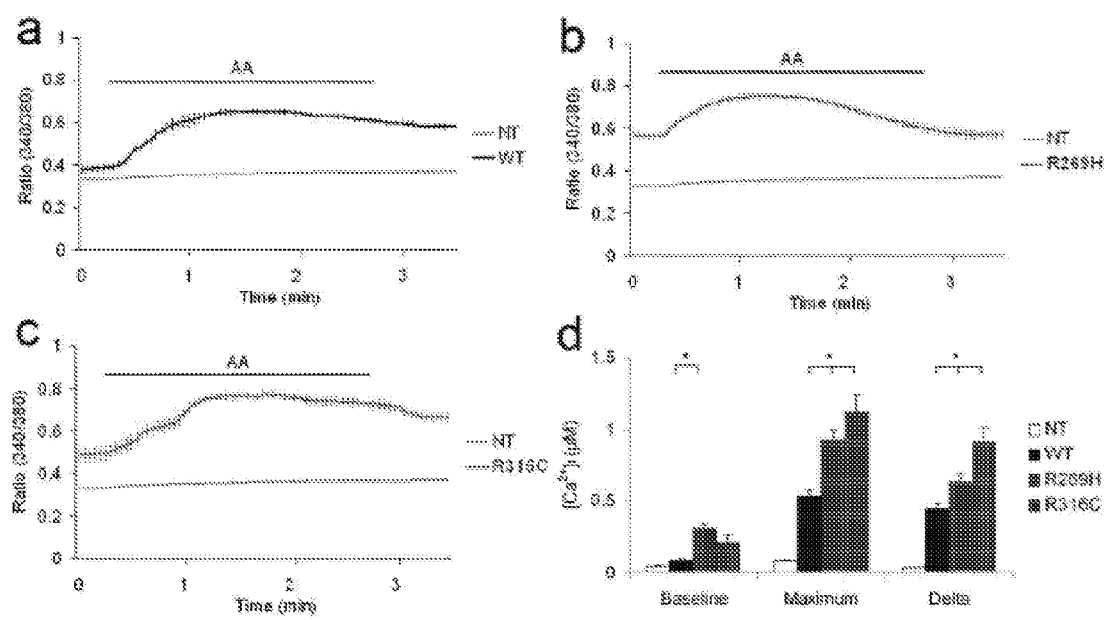
FIG. 10 shows graphs depicting the effect of mutations on TRPV4 activity when stimulated with arachidonic acid. Effect of stimulation with arachidonic acid (AA, 10 μM) on internal fluorescence ratio in WT-TRPV4 (a), R269H (b) and R316C (c) transfected HEK293 cells. (d) Application of 10 μM AA induced an increase in $[Ca^{2+}]_i$. Average increases, basal and maximum values are given.

The TRPV4 channel responds to a variety of stimuli (Nilius et al. Physiol Rev 87, 165-217 (2007); herein incorporated by reference in its entirety). To test the potential effects of the mutations on calcium channel activity, the calcium channel activity of transiently transfected HEK293 cells was analyzed using internal Fura-2 fluorescence ratio (340/380) as an indicator of the intracellular Ca2+ levels, which depend on Ca2+ influx. Calcium levels of the transfected cells were examined in response to various stimuli, including TRPV4-specific agonist 4α-phorbol 12,13-didecanoate (4αPDD) (SEE FIG. 4), osmotic cell swelling (SEE FIG. 5), moderate heat (37° C.) (SEE FIG. 9) and endogenous agonist arachidonic acid (SEE FIG. 10). A consistent pattern of channel response to different stimuli was observed. First, in non-stimulus conditions, both wild-type and mutants revealed increased basal intracellular calcium levels when compared to the non-transfected cells. Second, the TRPV4 mutants displayed a significantly increased basal calcium levels over the wtTRPV4, suggesting an increased constitutive activity for the mutants. Finally, the maximum and net increase in calcium levels in the mutant TRPV4 transfected cells were significantly higher than those in the cells transfected with the wtTRPV4, when activated by all the stimuli tested, indicating that the mutations confer an increased channel activity (SEE FIGS. 4, 5, 9 and 10). The increased calcium channel activity was inhibited by TRPV antagonist ruthenium red.

Figure 6:
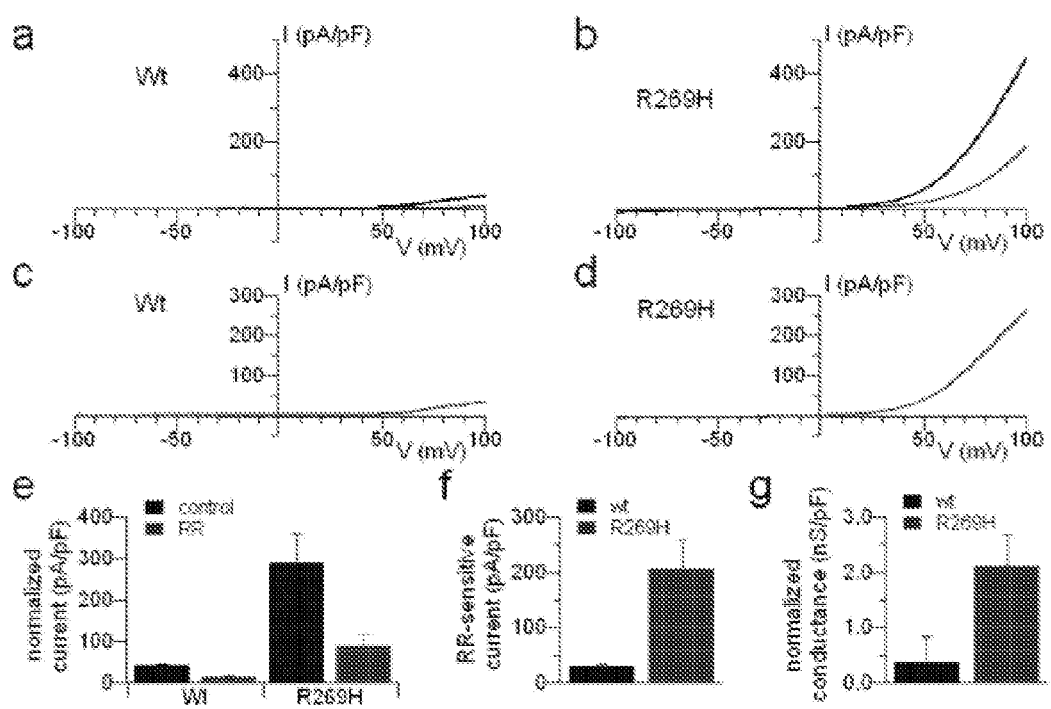
FIG. 6 shows graphs depicting whole cell recordings of TRPV4 currents from transfected HEK293 cells. (a, b) Voltage clamp recordings of the currents elicited by a slow voltage ramp (from −100 to 100 mV, 600 ms) in control condition (black traces) and in the presence of 20 μM ruthenium red (red traces) in cells expressing wtTRPV4 (a) or TRPV4-R269H (b) channels. (c, d) Ruthenium red-sensitive current (obtained by digital subtraction) in cells expressing wtTRPV4 (c) and TRPV4-R269H (d). (e) Plot summarizing the amount of current (normalized to capacitance) recorded at +100 mV in control conditions (black bars) and in the presence of ruthenium red (red bars) in cells expressing the wild type and mutated channels. (f) Plot summarizing the size of the ruthenium red-sensitive current in cells expressing the two channel types. (g) The ruthenium red-sensitive current was transformed into conductance. The conductance of TRPV4R269H expressing cells was ~6 times larger (0.35±0.5 in wild type and 2.1±0.6 in the mutant, 9 and 6 cells, respectively).

The effect of the CMT2C-linked mutation (TRPV4R269H) on the electrophysiological properties of TRPV4 was examined. Whole-cell patch-clamp recordings were obtained from transiently transfected HEK293 cells. While non-transfected cells had only small basal currents that did not show TRPV4 rectification, cells transfected either with the wtTRPV4 or the TRPV4R269H mutant channel exhibited large, outward rectifying basal currents (SEE FIGS. 6a and 6b). Addition of the TRPV blocker ruthenium red to the bath dramatically reduced the currents (SEE FIGS. 6a and 6b); the ruthenium red-sensitive component was then obtained by offline digital subtraction (SEE FIGS. 6c and 6d). These data show that most of the basal current in the transfected cells was actually mediated by TRPV4 channels (SEE FIG. 6e). Consistent with the calcium imaging data, the ruthenium red-sensitive TRPV4 conductance was larger in cells expressing the CMT2C-linked mutant compared to wtTRPV4 (at 100 mV the normalized conductance of the ruthenium red-sensitive component was 0.354±0.47 and 2.105±0.57 nS/pF for cells expressing the wild-type and mutated channels, respectively (SEE FIG. 6g). Consistent with previous findings (Wissenbach et al. *FEBS Lett* 485, 127-34 (2000); herein incorporated by reference in its entirety), it was also observed that about half of the wild type (22/47) and mutant (15/27) TRPV4-transfected HEK293 cells did not show rectifying TRPV4 currents.

TRPV4 is a vanilloid receptor-related transient receptor potential channel, and plays an important role in neural signaling (Pedersen et al. Cell Calcium 38, 233-52 (2005); Liedtke. Ann NY Acad Sci 1144, 42-52 (2008); herein incorporated by reference in their entireties). Two missense mutations (R616Q and V620I) of TRPV4 have been identified in 2 families with brachyolmia, and six missense mutations have been found in spondylometaphyseal dysplasia (SMD) Kozlowski type (SMDK), and two missense mutations in metatropic dysplasia, respectively (Rock et al. Nat Genet 40, 999-1003 (2008); Krakow, D. et al. Am J Hum Genet 84, 307-15 (2009); herein incorporated by reference in its entirety). The brachyolmia, SMDK and metatropic dysplasia are autosomal dominant dysplasias of the bones with variable severity. Among eight skeletal dysplasia-linked mutations tested in vitro, seven had an increased basal calcium channel activity, indicating that a "gain of function" mechanism, and an increase in calcium channel activity, underlies the skeletal dysplasias. Further indicating such a gain of function mutations is the observation that overexpression of mouse wild-type TRPV4 in zebra fish caused marked shortening and curvature of the axial skeleton (Wang, Y. et al. *J Biol Chem* 282, 36561-70 (2007); herein incorporated by reference in its entirety).

Some patients in the SPSMA family also presented variable skeletal abnormalities in addition to neuromuscular phenotypes. The skeletal abnormalities include congenital hip dysplasia, scoliosis, smaller hands with clinodactyly, and one arm or leg shorter than the other. Identification of the TRPV4-R316C mutation in the SPSMA family indicates that the TRPV4-R316C share a common property with other skeletal dysplasia-linked mutants in triggering skeletal abnormalities, and another distinct property with CMT2C-linked TRPV4-R269H in triggering neuropathic phenotypes. Thus, indicating that the SPSMA-linked TRPV4-R316C has two different properties that bridge these two clinicaly distinct groups of disorders, i.e. skeletal dysplasias and peripheral neuropathies.

Sensory impairment was shown in some cases with CMT2C, but was not obvious in most of the patients with SPSMA, except for reduced vibratory sense at 256 Hz in the feet in some SPSMA patients (DeLong & Siddique. Arch Neurol 49, 905-8 (1992); Dyck, P. J. et al. Ann Neurol 35, 608-15 (1994); herein incorporated by reference in their entireties). However, experiments conducted during development of embodiments of the present invention demonstrates that mutations in the same gene can cause distinct phenotypes or a spectrum of related phenotypes as in CMT and hereditary motor neuropathy (HMN). For examples, mutations in the GARS can cause CMT2D and dHMN522; mutations in the HSPB1 lead to CMT2F and dHMN2B23; mutations in HSPB8 result in CMT2L7 and dHMN2A6. These phenomena suggest that other genetic and environmental factors may modulate the phenotype.

TRPV4-R316C and TRPV4-R269H mutants have increased basal and maximum calcium channel activities compared to the wtTRPV4. Although the present invention is not limited to any particular mechanism of action and an understanding of the mechanism of action is not necessary to practice the present invention, experiments conducted during development of embodiments of the present invention indicate a "gain of function", rather than a "loss of function" mechanism is related to peripheral neuropathies. This is supported by observations that mice lacking TRPV4 do not show apparent neuromuscular abnormalities (Liedtke & Friedman. Proc Natl Acad Sci USA 100, 13698-703 (2003); Suzuki et al. J Biol Chem 278, 22664-8 (2003); herein incorporated by reference in their entireties). TRPV4 expression and/or function can be regulated by other auxiliary proteins such as OS-9, WNK4, AQP5 and the AIP4 ubiquitin ligas (Wang, Y. et al. J Biol Chem 282, 36561-70 (2007); Fu et al. Am J Physiol Renal Physiol 290, F1305-14 (2006); Liu, X. et al. J Biol Chem 281, 15485-95 (2006); Sidhaye et al. Proc Natl Acad Sci USA 103, 4747-52 (2006); Wegierski et al. EMBO J 25, 5659-69 (2006); herein incorporated by reference in their entireties). It has been demonstrated that PACSIN3 strongly inhibits the basal activity of TRPV4 and its activation by cell swelling and heat, but not by 4αPDD. Specific mutations of proline residues near the first ARD in the N-terminus of TRPV4 abolish binding of PACSIN3 and render the channel insensitive to PACSIN3-induced inhibition (D'Hoedt, D. et al. *J Biol Chem* 283, 6272-80 (2008); herein incorporated by reference in its entirety). TRPV4 is widely expressed in diverse cells, but the TRPV4-R269H and TRPV4-R316C mutations prominently affect axons of lower motor neurons.

Experimental

Patients and Samples.

This study has been approved by the local institutional review boards. DNA and other samples were taken after obtaining written informed consent. This study included a large New England family of French-Canadian origin with SPSMA and an American family of English and Scottish descent with CMT2C described previously.

Genetic Analysis.

Genomic DNA was extracted from whole peripheral blood, transformed lymphoblastoid cell lines or available tissues by standard methods (Qiagen, Valencia, Calif.). Intronic primers covering sequences of interest (such as coding exons) were designed at least 50 bp away from the intron/exon boundaries. When a PCR product was over 500 bp, multiple overlapping primers were designed with an average of 50 bp overlap. Primers were designed with the help of an Oligo analyzer (IDT, IA) and ExonPrimer software (Institute of Human Genetics, Germany). Forty nanograms of genomic DNA were used for PCR amplification with high fidelity TaKaRa LA Taq™ (Takara, Japan). The amplification protocol consisted of the following steps: incubation at 95° C. for 1 min, 32 cycles of 95° C. (30 s), 58° C. (30 s) and 72° C. (1 min) and a final 5 min extension at 72° C. Unconsumed dNTPs and primers were digested with Exonuclease I and Shrimp Alkaline Phosphatase (ExoSAP-IT, USB, Ohio). When non-specific PCR amplification occurred, the PCR products were separated by 1.5% agarose gel and the specific PCR product was cut out from the gel and purified using QIAquick Gel Extraction Kit (QIAGEN Science, Maryland). For sequencing of a PCR product, fluorescent dye labeled single strand DNA was amplified with Beckman Coulter sequencing reagents (GenomeLab DTCS Quick Start Kit) followed by single pass bi-directional sequencing with CEQ™ 8000 Genetic Analysis System (Beckman Coulter, Calif.) (Northwestern University) or using dye termination chemistry with 3730x1 sequencer (Applied Biosystems, Foster City, Calif.) (Mayo Clinic).

Expression Vectors.

A full length human cDNA clone (IMAGE: 40125977) was used as a template. Two primers anchored with an XhoI (TRPV4-TP1) and BamHI (TRPV4-TP2) were used to amplify the full length coding sequence. The amplified fragment was cloned into plasmid vector pBluescript M13. The TRPV4 sequence was verified by direct sequencing. The R316C mutation was introduced into the plasmid vector by site-directed mutagenesis using a primer containing R316C mutation (TRPV3-R316C) and R269H was introduced using a primer containing R269H mutation (TRPV4-R269H). The XhoI/BamHI fragment containing wild-type TRPV4, TRPV4$^{R316c}$ or TRPV4$^{R269H}$ was released from the pBluescript M13 vector and cloned into the XhoI and BamHI sites of a dual expression vector pIRES2-ZsGreen1 (Clontech, Mountain View, Calif.).

Expression of Wild-Type and Mutant TRPV4.

Human embryonic kidney cells (HEK293) were grown on collagen-coated glass coverslips in Dulbecco's modified Eagle's medium containing 10% (v/v) human serum, 2 mM L-glutamine, 2 U/ml penicillin, and 2 mg/ml streptomycin at 37° C. in a humidity-controlled incubator with 5% $CO_2$. The cells were transiently transfected with expression vectors, wild-type TRPV4, TRPV4$^{R316c}$ or TRPV4$^{R269H}$ using Lipofectamine 2000 (Invitrogen).

Confocal Microscopy.

HEK293 cells were seeded on collagen-coated coverslides 24 hours prior to transfection. Twenty-four hours after transfection, the cells were fixed with 3% paraformaldehyde and 0.02% glutaldehyde for 15 minutes. Ice-cold methanol was used to permeablize cells. Rabbit anti-TRPV4 antibody (1:50, Chemicon, Temecula, Calif.) and mouse anti-cadherin (1:200, Abcam, Cambridge, Mass.) were used as primary antibodies. Alexa Fluor 555 goat anti-mouse (1:500, Invitrogen) and Alex 633 goat anti-rabbit (1:250, Invitrogen) were used as secondary antibodies. Digital images were captured and analyzed with Carl Zeiss LSM 510 META laser scanning confocal microscopes.

Calcium Imaging and Intracellular $Ca^{2+}$ Measurements.

Intracellular free calcium concentration was measured using digital video microfluorimetry. Twenty-four hours after transfection, cells were rinsed briefly with HEPES buffer (120 mM NaCl, 5.4 mM KCl, 1.6 mM $MgCl_2$, 1.8 mM $CaCl_2$, 11 mM glucose, and 25 mM HEPES, pH 7.2), and loaded with 4 μM fura-2 AM (Molecular Probes) in HEPES buffer for 30 min at room temperature. Cultures were then rinsed and kept in the dark in HEPES buffer at room temperature for an additional 30 min to allow for complete dye de-esterification. The coverslips were then mounted on the stage of a Nikon Diaphot inverted epifluorescence microscope equipped for digital fluorescence microscopy. After excitation at 340 nm ($Ca^{2+}$-bound) and 380 nm ($Ca^{2+}$-free) fluorescence was digitally monitored at 520 nm. $F_{340}/F_{380}$ ratios were collected before and during treatment with 10 μM arachidonic acid, 2 μM 4 alpha-phorbol 12,13-didecanoate (4αPDD), or 200 mOsm hypotonic saline (HTS) using MetaFluor software (Universal Imaging Corporation). For temperature activation, cells were incubated in HEPES at 14° C., and stimulated with HEPES at 37° C. Ruthenium red (20 μM) was used to block the effects of these stimuli. Measurements were calibrated using the Grynkiewicz equation[31]. Values for $R_{min}$ and $R_{max}$ were determined by applying $Ca^{2+}$-free solution and high $Ca^{2+}$ containing solution in the presence of 5 μM ionomycin, respectively. The dissociation constant ($K_d$) of 224 nM for fura-2 AM was used for calculations. Imaging experiments were performed at room temperature, unless otherwise stated. Two tailed unpaired Student's t-test ($p<0.05$) was used for statistical analysis.

Electrophysiology.

Whole cell voltage clamp recordings were performed to HEK293 cells transiently transfected with wild-type or R269H TRPV4 cDNA. For experiments with ruthenium red blockage, cells were incubated with ruthenium red (10 μm) after transfection. Similar GFP-fluorescent cells were selected for experiments. Patch pipettes were pulled from WPI (Sarasota, Fla.) glass (PG10-165) using a horizontal puller (P97, Sutter, Novato, Calif.) and had a resistance of 2 to 3 MΩ when filled with internal solution consisting of (in mM): CsCl 140, $MgCl_2$ 2, EGTA 10, $Na_2ATP$ 2, NaGTP 0.1, HEPES 10, pH 7.3 adjusted with CsOH. The series resistance was 4 to 14 MΩ and was compensated between 65 and 75%. The extracellular solution consisted of (in mM): NaCl 100, KCl 6, $MgCl_2$ 2, $CaCl_2$ 1.5, Glucose 10, HEPES 10, pH 7.38 adjusted with NaOH, ~315 mOsm adjusted with sucrose. Whole cell currents were recorded using an Axopatch 200B amplifier (Molecular Devices). Cells were held at −30 mV and currents were elicited by slow voltage ramps (from −100 mV to +100 mV, 0.6 sec duration), filtered at 5 KHz and sampled at 10 KHz. Drugs were bath-applied at a rate of ~4 ml/min. The current density was determined by normalizing the current to the cell capacitance measured in voltage clamp using a −5 mV square pulse from a holding potential of −30 mV. Ruthenium red was prepared in a 20 mM stock solution (in water) and stored at 2-4° C. Working solutions were prepared freshly daily and were bath applied. After drug application the dish was discarded even if complete wash-out of the drug was obtained.

The present invention is not limited to any particular mechanism of action of TRPV4 and/or mutant forms thereof, and an understanding of the mechanism of action is not necessary to practice the present invention. Although the invention has been described in connection with specific preferred embodiments, it should be understood that the invention as claimed should not be unduly limited to such specific embodiments. Various modification and variation of the described methods and compositions of the invention will be apparent to those skilled in the art without departing from the scope and spirit of the invention. Indeed, various modifications of the described modes for carrying out the invention understood by those skilled in the relevant fields are intended to be within the scope of the following claims. All publications and patents mentioned in the present application and/or listed below are herein incorporated by reference.

REFERENCES

1. DeLong, R. & Siddique, T. A large New England kindred with autosomal dominant neurogenic scapuloperoneal amyotrophy with unique features. *Arch Neurol* 49, 905-8 (1992).
2. Dyck, P. J. et al. Hereditary motor and sensory neuropathy with diaphragm and vocal cord paresis. *Ann Neurol* 35, 608-15 (1994).
3. Isozumi, K. et al. Linkage of scapuloperoneal spinal muscular atrophy to chromosome 12q24.1-q24.31. *Hum Mol Genet* 5, 1377-82 (1996).
4. Klein, C. J. et al. The gene for HMSN2C maps to 12q23-24: a region of neuromuscular disorders. *Neurology* 60, 1151-6 (2003).
5. McEntagart, M. E. et al. Confirmation of a hereditary motor and sensory neuropathy IIC locus at chromosome 12q23-q24. *Ann Neurol* 57, 293-7 (2005).
6. Irobi, J. et al. Hot-spot residue in small heat-shock protein 22 causes distal motor neuropathy. *Nat Genet* 36, 597-601 (2004).
7. Tang, B. S. et al. Small heat-shock protein 22 mutated in autosomal dominant Charcot-Marie-Tooth disease type 2L. *Hum Genet* 116, 222-4 (2005).
8. Ramser, J. et al. Rare missense and synonymous variants in UBE1 are associated with X-linked infantile spinal muscular atrophy. *Am J Hum Genet* 82, 188-93 (2008).
9. Quinzii, C. M. et al. X-linked dominant scapuloperoneal myopathy is due to a mutation in the gene encoding four-and-a-half-LIM protein 1. *Am J Hum Genet* 82, 208-13 (2008).
10. Liedtke, W. et al. Vanilloid receptor-related osmotically activated channel (VR-OAC), a candidate vertebrate osmoreceptor. *Cell* 103, 525-35 (2000).
11. Strotmann, R., Harteneck, C., Nunnenmacher, K., Schultz, G. & Plant, T. D. OTRPC4, a nonselective cation channel that confers sensitivity to extracellular osmolarity. *Nat Cell Biol* 2, 695-702 (2000).
12. Wissenbach, U., Bodding, M., Freichel, M. & Flockerzi, V. Trp12, a novel Trp related protein from kidney. *FEBS Lett* 485, 127-34 (2000).
13. Jin, X., Touhey, J. & Gaudet, R. Structure of the N-terminal ankyrin repeat domain of the TRPV2 ion channel. *J Biol Chem* 281, 25006-10 (2006).
14. Phelps, C. B., Huang, R. J., Lishko, P. V., Wang, R. R. & Gaudet, R. Structural analyses of the ankyrin repeat domain of TRPV6 and related TRPV ion channels. *Biochemistry* 47, 2476-84 (2008).
15. Arniges, M., Fernandez-Fernandez, J. M., Albrecht, N., Schaefer, M. & Valverde, M. A. Human TRPV4 channel splice variants revealed a key role of ankyrin domains in multimerization and trafficking *J Biol Chem* 281, 1580-6 (2006).
16. Nilius, B., Owsianik, G., Voets, T. & Peters, J. A. Transient receptor potential cation channels in disease. *Physiol Rev* 87, 165-217 (2007).
17. Pedersen, S. F., Owsianik, G. & Nilius, B. TRP channels: an overview. *Cell Calcium* 38, 233-52 (2005).
18. Liedtke, W. Molecular mechanisms of TRPV4-mediated neural signaling. *Ann N Y Acad Sci* 1144, 42-52 (2008).
19. Rock, M. J. et al. Gain-of-function mutations in TRPV4 cause autosomal dominant brachyolmia. *Nat Genet* 40, 999-1003 (2008).
20. Krakow, D. et al. Mutations in the gene encoding the calcium-permeable ion channel TRPV4 produce spondylometaphyseal dysplasia, Kozlowski type and metatropic dysplasia. *Am J Hum Genet* 84, 307-15 (2009).
21. Wang, Y. et al. OS-9 regulates the transit and polyubiquitination of TRPV4 in the endoplasmic reticulum. *J Biol Chem* 282, 36561-70 (2007).
22. Antonellis, A. et al. Glycyl tRNA synthetase mutations in Charcot-Marie-Tooth disease type 2D and distal spinal muscular atrophy type V. *Am J Hum Genet* 72, 1293-9 (2003).
23. Evgrafov, O. V. et al. Mutant small heat-shock protein 27 causes axonal Charcot-Marie-Tooth disease and distal hereditary motor neuropathy. *Nat Genet* 36, 602-6 (2004).
24. Liedtke, W. & Friedman, J. M. Abnormal osmotic regulation in trpv4−/− mice. *Proc Natl Acad Sci USA* 100, 13698-703 (2003).
25. Suzuki, M., Mizuno, A., Kodaira, K. & Imai, M. Impaired pressure sensation in mice lacking TRPV4. *J Biol Chem* 278, 22664-8 (2003).
26. Fu, Y., Subramanya, A., Rozansky, D. & Cohen, D. M. WNK kinases influence TRPV4 channel function and localization. *Am J Physiol Renal Physiol* 290, F1305-14 (2006).
27. Liu, X. et al. A role for AQP5 in activation of TRPV4 by hypotonicity: concerted involvement of AQP5 and TRPV4 in regulation of cell volume recovery. *J Biol Chem* 281, 15485-95 (2006).
28. Sidhaye, V. K. et al. Transient receptor potential vanilloid 4 regulates aquaporin-5 abundance under hypotonic conditions. *Proc Natl Acad Sci USA* 103, 4747-52 (2006).
29. Wegierski, T., Hill, K., Schaefer, M. & Walz, G. The HECT ubiquitin ligase AIP4 regulates the cell surface expression of select TRP channels. *EMBO J* 25, 5659-69 (2006).

30. D'Hoedt, D. et al. Stimulus-specific modulation of the cation channel TRPV4 by PACSIN 3. *J Biol Chem* 283, 6272-80 (2008).

31. Grynkiewicz, G., Poenie, M. & Tsien, R. Y. A new generation of Ca2+ indicators with greatly improved fluorescence properties. *J Biol Chem* 260, 3440-50 (1985).

We claim:

1. An in vitro method of detecting a mutation in a TRPV4 nucleic acid in a biological sample comprising: (a) obtaining a biological sample from a subject; (b) contacting a TRPV4 nucleic acid from the biological sample with an oligonucleotide comprising a fragment of a TRPV4 nucleic acid that specifically binds to a TRPV4 nucleic acid encoding a cysteine at position 316 of the TRPV4 protein and which does not bind to a TRPV4 nucleic acid encoding an arginine at position 316 of the TRPV4 protein; or with an oligonucleotide comprising a fragment of a TRPV4 nucleic acid that specifically binds to a TRPV4 nucleic acid encoding a histidine at position 269 of the TRPV4 protein and which does not bind to a TRPV4 nucleic acid encoding an arginine at position 269 of the TRPV4 protein; and (c) detecting hybridization of the TRPV4 nucleic acid from the biological sample with the oligonucleotide, wherein hybridization is indicative of a mutation in a TRPV4 nucleic acid in the biological sample, and wherein the mutation encodes for a TRPV4-R269H or TRPV4-R316C mutation.

2. The method of claim 1, wherein the method further comprises amplifying the TRPV4 nucleic acid with a pair of primers configured to amplify all or a portion of the TRPV4 nucleic acid that encodes amino acids 269 and 316 of the TRPV4 protein.

* * * * *